United States Patent
Yang

(12) United States Patent (10) Patent No.: US 7,762,682 B2
Yang (45) Date of Patent: Jul. 27, 2010

(54) CONTAINER DEVICE

(76) Inventor: Chin-Sheng Yang, 4F., No. 26, Lane 358, Yung-An St., Tainan City (TW)

( * ) Notice: Subject to any disclaimer, the term of this patent is extended or adjusted under 35 U.S.C. 154(b) by 0 days.

(21) Appl. No.: 12/241,100

(22) Filed: Sep. 30, 2008

(65) Prior Publication Data

US 2009/0103286 A1 Apr. 23, 2009

(30) Foreign Application Priority Data

Oct. 19, 2007 (TW) ............................... 96217580 U

(51) Int. Cl.
*F21V 33/00* (2006.01)
(52) U.S. Cl. ..................... 362/155; 362/101; 362/276
(58) Field of Classification Search ................ 362/96, 362/101, 154, 295, 318, 806, 811; 446/485; 473/57

See application file for complete search history.

(56) References Cited

U.S. PATENT DOCUMENTS

| 4,507,716 A | * | 3/1985 | Benedict, Jr. | 362/295 |
| 5,067,060 A | * | 11/1991 | Sieracki | 362/101 |
| 5,624,177 A | * | 4/1997 | Rosaia | 362/101 |
| 6,467,926 B1 | * | 10/2002 | Tee et al. | 362/101 |

* cited by examiner

*Primary Examiner*—Ali Alavi
(74) *Attorney, Agent, or Firm*—Leong C. Lei

(57) ABSTRACT

The container device contains a base member, a circuit member housed inside the base member, and an illuminative member and a storage member, both on top of the base member. The storage member is for holding seasoning or fragrance. The illuminative member has a transparent hollow casing filled with a fluid of appropriate viscosity. The circuit member contains at least a light generating element and a switch element that is turned on and off by touching or shaking the container device. When the container device is touched by hand or shook, the switch element is turned on and the light generating elements are lit to provide illumination through the transparent illuminative member.

1 Claim, 5 Drawing Sheets

CONTAINER DEVICE

(a) TECHNICAL FIELD OF THE INVENTION

The present invention generally relates to tabletop or desktop containers, and more particularly to a self-illuminative container device for holding seasoning or fragrance.

(b) DESCRIPTION OF THE PRIOR ART

Pepper mill and salt shaker are common containers for seasonings on a kitchen or dinner table. They have been designed with various shapes to make dinning a more pleasant experience. Similarly, perfume bottles are designed with exotic shapes so that they are not only containers but also a decoration to the dressing table.

SUMMARY OF THE INVENTION

A novel container device for seasoning and fragrance is provided herein which provides self-illuminative lighting effect to make them more appealing. The container device contains a base member, a circuit member housed inside the base member, and an illuminative member and a storage member, both on top of the base member. The storage member is for holding seasoning or fragrance. The illuminative member has a transparent hollow casing filled with a fluid of appropriate viscosity. The circuit member contains at least a light generating element and a switch element that is turned on and off by touching or shaking the container device. When the container device is touched by hand or shook, the switch element is turned on and the light generating elements are lit to provide appealing lighting effect through the transparent illuminative member.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
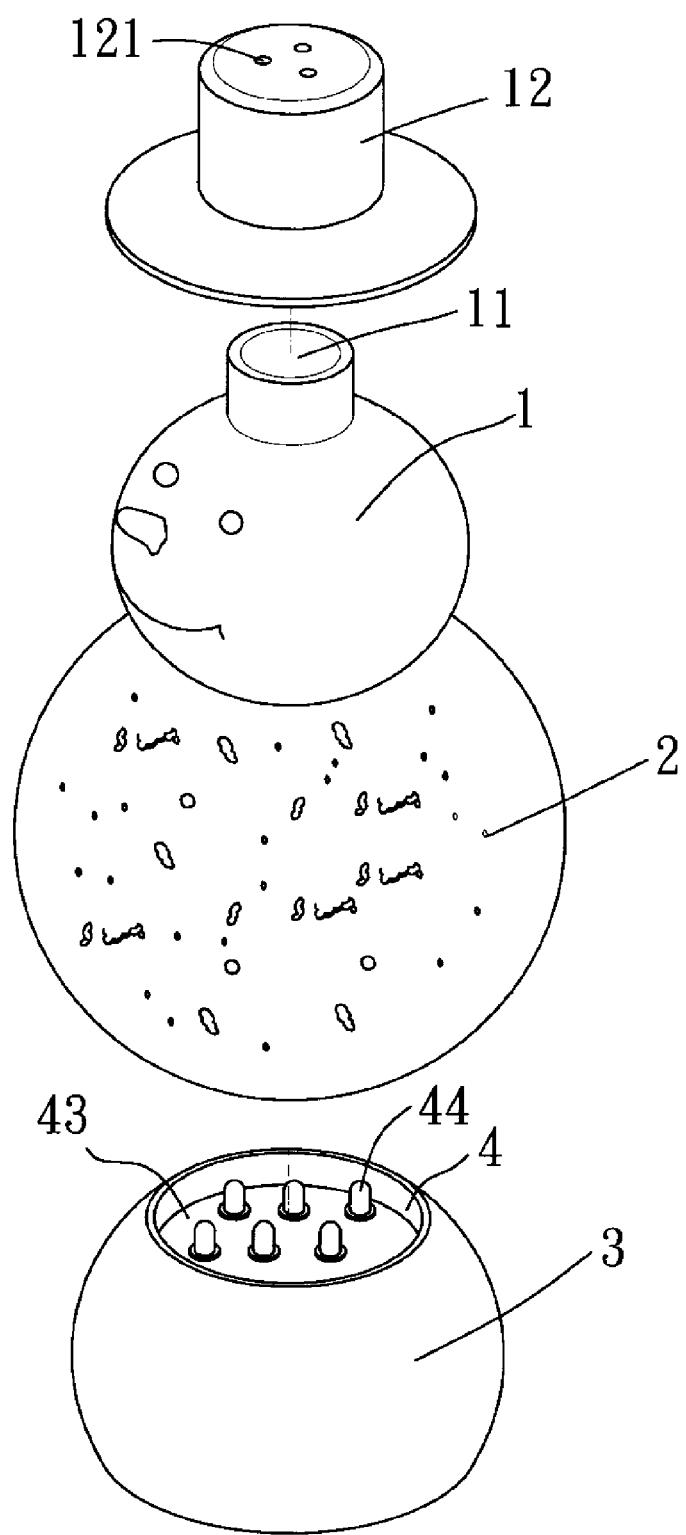
FIG. 1 is a perspective diagram showing a container device according a first embodiment of the present invention.
Figure 2:
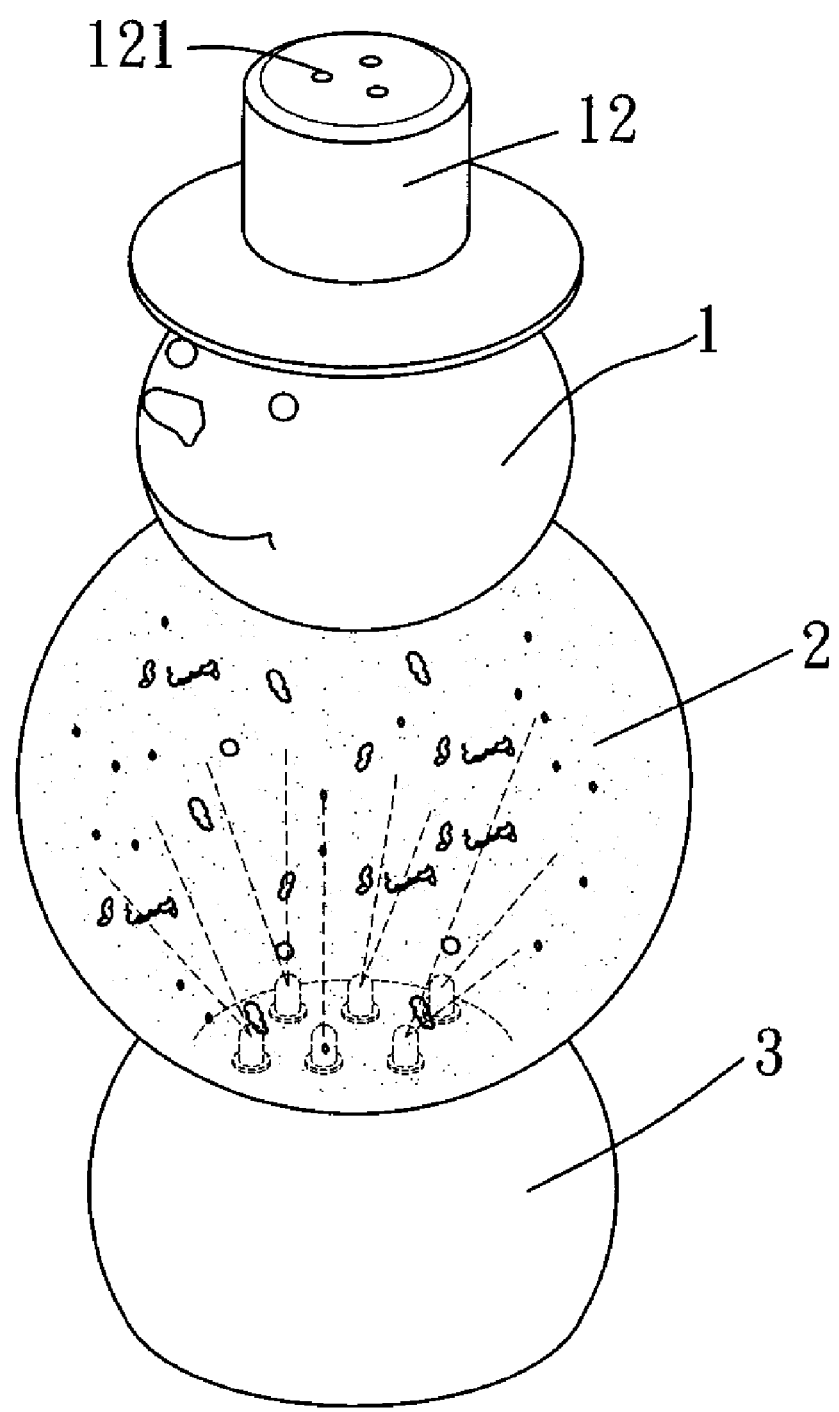
FIG. 2 is a perspective diagram showing the container device of FIG. 1 after its assembly.

As shown in FIGS. 1 and 2, a container device according to a first embodiment of the present invention contains a base member 3, a circuit member 4 housed inside the base member 3, and an illuminative member 2 and a storage member 1 stacked on a top opening of the base member 3 in this order.

The storage member 1 has a hollow spherical or cylindrical chamber with a top opening 11 which could be further covered by a cap element 12 or plugged by a plug element 13.

The illuminative member 2 has a transparent hollow casing filled with a fluid of appropriate viscosity.

The top opening of the base member 3 exposes an indentation of the base member where the circuit member 4 is positioned and sealed by the illuminative member 2.

The circuit member 4 contains a power element 42 for the provision of electricity, a circuit element 43, at least a light generating element 44, and a switch element 41 that is turned on and off by touching or shaking the container device. The details of the circuit member 4 should be quite straightforward to people of related arts and are omitted here.

Figure 3:
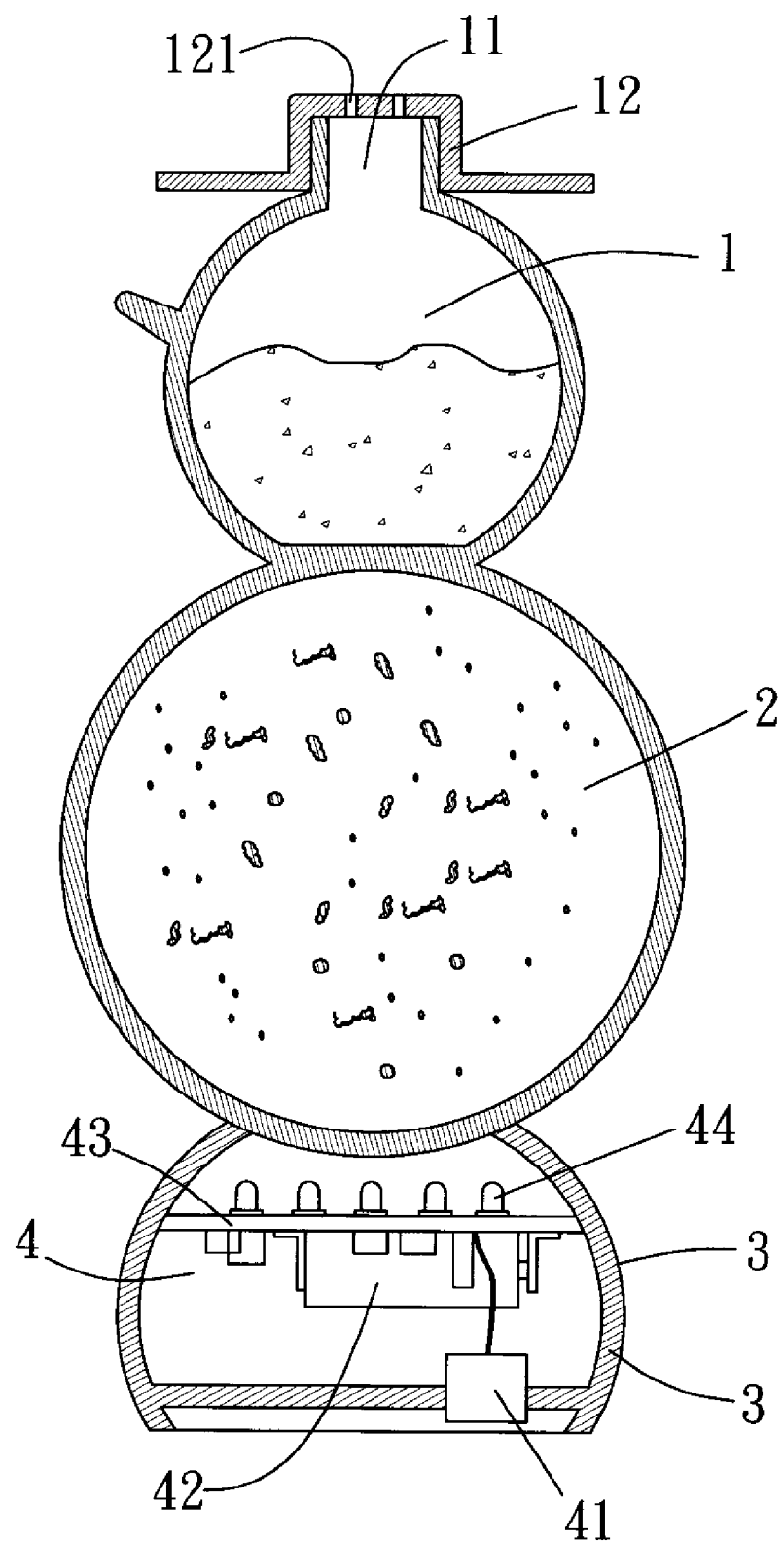
FIG. 3 is a sectional diagram showing the container device of FIG. 1.

As shown in FIG. 3, the light generating elements 44 are arranged on a top side of the flat circuit element 43 so that their light projects upward towards the top opening of the base member 3 and the illuminative member 2. The switch element 41 is connected to the circuit element 43. The power element 42 which is a battery is attached to a bottom side of the circuit element 43 to provide electricity to the circuit element 43 and the light generating elements 44. The storage member 1 could have salt, pepper, etc. placed in the chamber. The cover element 12 therefore has perforations 121. In other words, the container device functions as a pepper mill or a salt shaker. When the container device is touched by hand or shook, the switch element 41 is turned on and the light generating elements 44 are lit to provide illumination through the transparent illuminative member 2.

Figure 4:
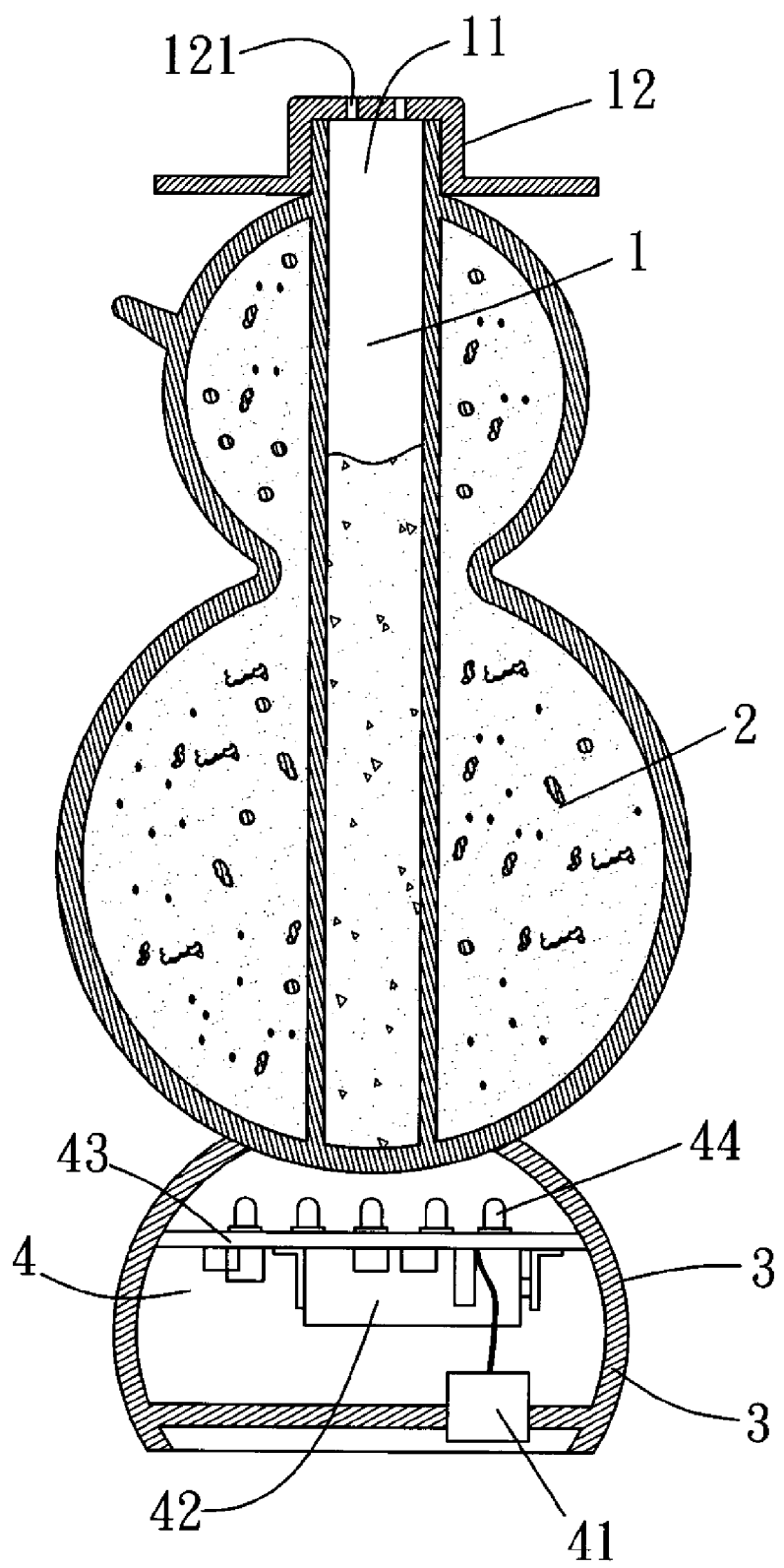
FIG. 4 is a sectional diagram showing a container device according a second embodiment of the present invention.

As shown in FIG. 4, a container device according to a second embodiment of the present invention has the storage member 1 housed inside the illuminative member 2. Again, the storage member 1 could have salt, pepper, etc. placed in the chamber. When the container device is touched by hand or shook the switch element 41 is turned on and the light generating elements 44 are lit to provide appealing lighting effect through the transparent illuminative member 2.

Figure 5:
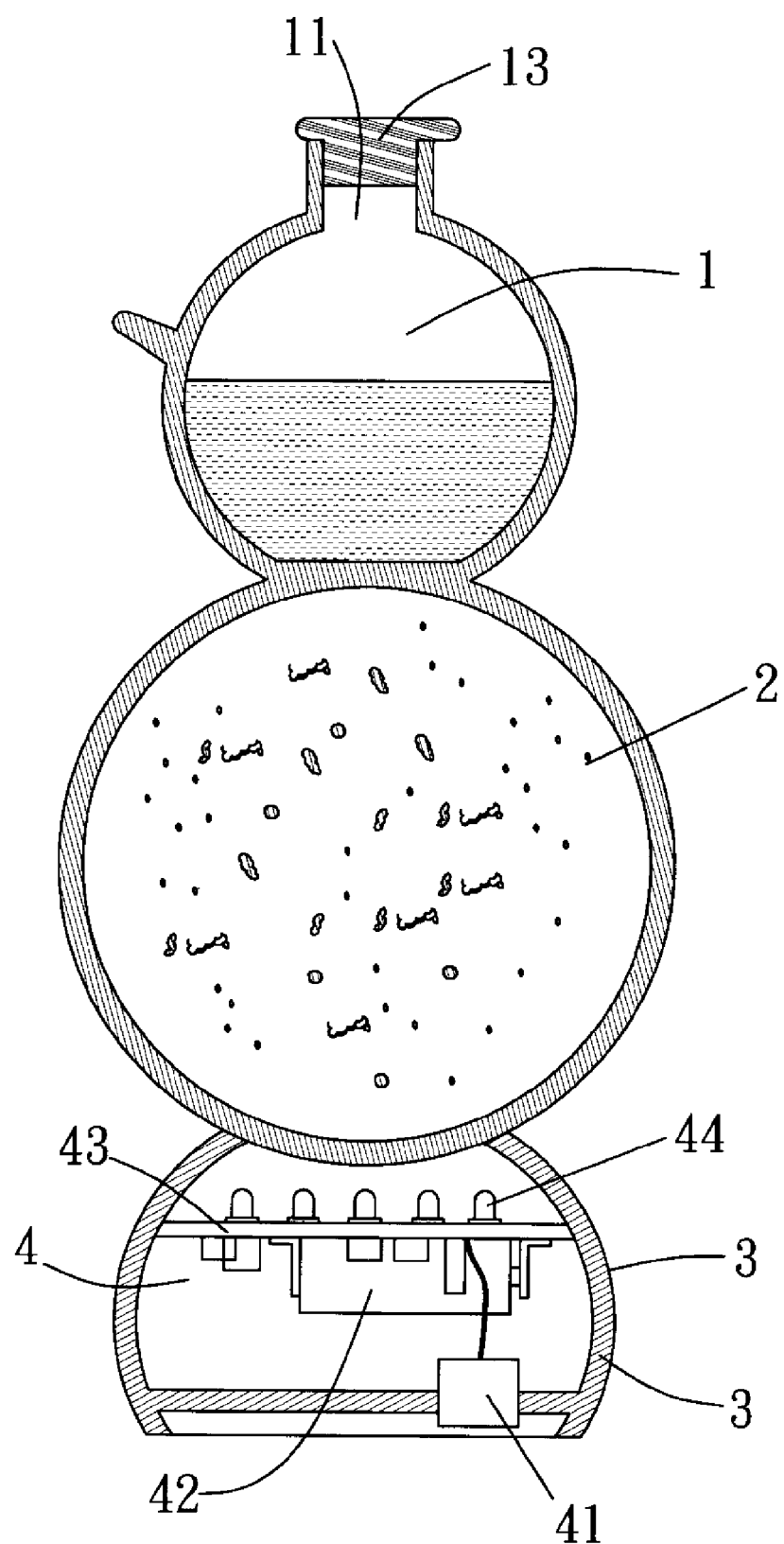
FIG. 5 is a sectional diagram showing a container device according a third embodiment of the present invention.

As shown in FIG. 5, a container device according to a third embodiment of the present invention has fragrant fluid in the chamber of the storage member 1. The top opening of the storage member 1 is therefore sealed by a plug element 13. Again, when the container device is touched by hand or shook, the switch element 41 is turned on and the light generating elements 44 are lit to provide appealing lighting effect through the transparent illuminative member 2.

Additionally, spangles or glittery powder could be dispersed in the fluid of the illuminative member 2 so that, when the light generating elements 44 are lit, the reflection of the spangles or the powder provides a dazzling visual effect.

As described above, the container device could be used as a pepper mill or a salt shaker on the dinner table and, with its interesting visual effect, could make dinning a more pleasant experience. The container device could also be used to hold vaporizable fragrant liquid and therefore used as an air refresher. The container device then could be placed in the bathroom or anywhere inside a house. The storage member of the container device could also be used to hold perfume.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A container device comprising:
   a base member having a top opening exposing an indentation of said base member;
   an illuminative member positioned atop said base member and sealing said top opening of said base member, said illuminative member having a hollow transparent casing filled with a viscous fluid, said fluid being dispersed with a plurality of spangles;
   a circuit member housed inside said indentation of said base member, said circuit member having at least a light generating element whose light projects towards said illuminative member, said circuit member turning on and off said light generating element by touching or shaking said container device, said circuit member further having a power element for provision of electricity and a switch element for sensing hand touch or vibration of said container device;
   a storage member being a tubular member housed inside said illuminative member; and
   a cap element adapted to cover a top opening of said storage member and provided with a plurality of perforations;
   wherein, when said container device is touched by hand or shook, said light generating element is lit to provide illumination through said illuminative member.

* * * * *